United States Patent [19]

Beachley, Jr.

[11] Patent Number: 4,710,575

[45] Date of Patent: Dec. 1, 1987

[54] BISNEOPENTYL ALKYL ORGANOMETALLIC COMPOUNDS AND METHODS OF PREPARING SAME

[75] Inventor: Orville T. Beachley, Jr., Buffalo, N.Y.

[73] Assignee: The Research Foundation of State University of New York, Albany, N.Y.

[21] Appl. No.: 894,571

[22] Filed: Aug. 8, 1986

Related U.S. Application Data

[63] Continuation-in-part of Ser. No. 673,836, Nov. 21, 1984, Pat. No. 4,621,147.

[51] Int. Cl.$^4$ ............................................... C07F 5/00
[52] U.S. Cl. ........................................................ 556/1
[58] Field of Search ............................................ 556/1

[56] References Cited

U.S. PATENT DOCUMENTS 4,101,568  7/1978  Malpass et al. .
4,148,756  4/1979  Langer, Jr. ........................... 526/124
4,170,604  10/1979  Malpass et al. .

OTHER PUBLICATIONS

Chemical Abstracts 91, 20201h (1979).
Chemical Abstracts 65, 3994e (1966).
Mole et al., Organoaluminum Compounds, Elsevier Publ. Co., N.Y., pp. 54, 88 & 89 (1972).
Nesmeyanov et al., Methods of Elements—Organic Chem., North Holland Publ. Co., Amsterdam, vol. 1, pp. 386–387, 506, 507, 526–528, 398 and 450 (1967).

*Primary Examiner*—Helen M. S. Sneed
*Attorney, Agent, or Firm*—Omri M. Behr

[57]    ABSTRACT

In the manufacture of semiconductors it is desirable to make controlled deposits of certain phosphides or arsenides of trivalent metals such as gallium and indium. There are provided novel alkyl bisneopentyl derivatives of these metals whose stability and volatility characteristics makes them ideally suited for the above purpose.

3 Claims, No Drawings

BISNEOPENTYL ALKYL ORGANOMETALLIC COMPOUNDS AND METHODS OF PREPARING SAME

RELATED APPLICATIONS

This application is a continuation-in-part of my co-pending application, Ser. No. 673,836, filed Nov. 21, 1984, now U.S. Pat. No. 4,621,147.

BACKGROUND OF THE INVENTION

In the conventional preparation of semiconductors a predetermined amount of extremely pure metal phosphide or arsenide are laid down on the substrate crystal. The accepted mode of carrying out this process is to charge predetermined amounts of phosphine or arsine into a stream of hydrogen together with the appropriate amount of an organometallic compound. The said mixed gas stream is passed through a furnace at a predetermined temperature, said furnace containing the crystal on which deposition is desired. At the predetermined temperature, an elimination reaction will take place whereby the organic portion of the organometallic is eliminated and replaced by phosphorus or arsenic as is appropriate. In order for this reaction to take place properly and efficiently the organometallic utilized must be sufficiently stable under the furnace conditions that it does not decompose per se and yet it must be sufficiently reactive to permit the elimination reaction to occur substantially instantaneously when the gas stream enters the heated furnace area.

The organometallic should also be comparatively simple to prepare and, desirably, not be pyrophoric. That is to say, that should it accidently come into contact with air due to process errors, it would not spontaneously inflame.

Heretofore, the organic group used in the synthesis of these compounds has been the methyl group. However, the metalomethyls of this group are extremely volatile and pyrophoric. This handling disadvantage makes it desirable to provide alternative compounds.

The ethyl, isopropyl and isobutyl derivatives decompose too readily at elevated temperatures to permit the elimination reaction to take place in the proper manner.

In my copending application there are provided the trisneopentyl derivatives of gallium and indium. These have greater thermal stability and longer shelf life than other metalo-organic compounds of these metals. They are easier to prepare at lower cost of synthesis than the previously known compounds and moreover, lack pyrophoric character.

Furthermore, these compounds have a sufficient level of volatility to permit them to be utilized in the gas phase synthesis of the corresponding phosphides or arsenides, a procedure which is useful in the manufacture of various semiconductors containing the said phosphides and arsenides.

SUMMARY OF THE INVENTION

The novel bisneopentyl alkyl gallium and indium compounds of the present invention have equal stability to the corresponding trisneopentyl compounds but are more volatile.

The novel bisneopentyl organometallic compounds of the present inventon are readily simply prepared from the corresponding trisneopentyl compounds in accordance with a general procedure. The corresponding metal chloride is dissolved in diethyl ether and heated under reflux with 2 mols of the trisneopentyl compound. The resulting solution is reacted with an appropriate metalloalkyl, which is prepared in another diethyl ether solution in the conventional manner, by slowly adding the thus produced reagent to the metal bisneopentyl chloride solution. The reaction product is obtained in an ether solution from which the ether is removed and the pure product extracted with a hydrocarbon solvent.

DESCRIPTION OF THE PREFERRED EMBODIMENTS

Freshly prepared metal trisneopentyl is prepared in dry ethereal solvent. As the metal halide there may be utilized the chlorides, bromides and iodides. However, it is preferred to use the chloride. While any ether may be employed as a solvent, it is preferred from the point of view of expense and simplicity, to utilize diethyl ether.

While other lower alkyls may be used, methyl and ethyl are preferred.

The trisneopentyl metal is prepared in the manner disclosed in our copending application, which disclosure is incorporated by reference.

Stoichiometrically, the reaction requires two moles of metal trisneopentyl per mole of metal trihalide which may be chloro, bromo or iodo. Even small variations from stoichiometry will give rise to impure product.

The reactants are, suitably, heated under reflux in an ethereal solution, preferably in diethyl ether for from about 24 to about 72, suitably about 48 hours and the solution filtered to yield a solution of bisneopentyl metal halide.

The filtrate is then reacted with an metallo lower alkyl, suitably methyl or ethyl, preferably methyl. As a metal moiety, lithium is preferred, although Grignard moieties MgCl-, MgI- or MgBr- may be used.

The ethereal solution of the metal alkyl (suitably a substantially stoichiometric equivalent) is then slowly added to the bisneopentyl halide ether solution at $-15°$ C. to $+5°$ C. over a period of from about 5 to 25 minutes, suitably over a period of about 10 minutes under a dry inert atmosphere. Upon completion of addition the reaction mixture is stirred for a further 1 to about 4 hours again at ambient temperature.

As is not unusual in reactions of this type, a voluminous precipitate of magnesium or lithium halide is obtained. The ether is removed under reduced pressure and the product extracted with a hydrocarbon solvent, preferably a volatile solvent such as pentane which is then removed to yield a liquid product. The soluble fraction is then evacuated at room temperature for about 3 hours to remove last traces of ether or pentane. The reaction product is then finally purified by vacuum distillation at bath ca. 80° C. and head 55° C.

EXAMPLE I

Trisneopentylgallium

A flask charged with 9.578 g. (54.41 mmol) of freshly sublimed gallium trichloride dissolved in 250 ml. of dry diethyl ether (from sodium/benzophenone), was fitted with a condenser, mechanical stirrer and a pressure equalizing addition funnel. Under a cover of argon, 100 ml., 2.27M neopentyl magnesium chloride in diethyl ether solution (previously prepared from purified neopentyl chloride and magnesium turnings) was transferred to the addition funnel. The Grignard reagent was then added to the gallium trichloride solution over a period of 20 min. After the addition was complete, the reaction mixture was stirred at room temperature for 18 hours. The stirrer, condenser and addition funnel were replaced by stoppers and a Teflon valve adapter. The diethyl ether was then removed by vacuum distillation at room temperature. The crude product, a trisneopentylgallium etherate mixture, was isolated by vacuum distillation at 125° C. into a sidearm flask (cooled to −196° C.) attached to the reaction flask by means of an 85° elbow. This distillation must be continued for approximately 5 hours. The diethyl ether was then removed from stirred, crude trisneopentyl gallium by simple vacuum distillation at room temperature for 1 hour. The product was finally purified by vacuum distillation in a short path still at 59.5° C. (0.01 mm, static vacuum). The yield of purified trisneopentyl gallium was 14.04 g (49.58 mmol, 91.1% based on gallium trichloride).

In accordance with the above procedure, but using the corresponding bromides or iodides in place of chlorides with either or both reagents, the same product is obtained.

Trisneopentyl Gallium Properties

Colorless liquid, slightly volatile at 20° C. Anal. (Schwarzkopf Microanalytical Laboratory) Calcd: C, 63.63; H, 11.75. Found: C, 63.64; H, 11.68. $^1$H NMR ($C_6H_6$ (7.13) δ) 1.06 (s, 27H, $CCMe_3$); 1.01 (s, 6H $CH_2Ga$). Cyroscopic molecular weight, benzene solution, formula weight 283.2 (calc. m, obs MW) 0.0770, 275; 0.0610, 291; 0.0510, 304. IR (pure liquid cm$^{-1}$, relative intensity) 2950 vs, 2900 vs, 2860 vs, 2650 w, 1468 s, 1461 s, 1398 m, 1382 m, 1358 vs, 1229 s, 1132 m, 1095 m 1031 m, 1006 s, 928 w, 909 w, 735 m, 703 m, 610 m, 591 m 570 m, 460 sh, 450 m, 380 m, 310 m, 287 m. Trisneopentyl gallium is not pyrophoric but the compound is exceedingly sensitive to oxygen and water.

EXAMPLE II

Trisneopentylindium

A flask, charged with 29.13 g (58.3 mmol) of indium triiodide dissolved in 100 ml. of dry diethyl ether (from sodium/benzophenone) was fitted with a condenser, magnetic stir bar and a pressure equalizing addition funnel. Under a cover of argon, 100 ml., 2.32M neopentyl magnesium chloride in diethyl ether solution (previously prepared from purified neopentyl chloride and magnesium turnings) was transferred to the addition funnel. The Grignard reagent was then added to the indium triiodide solution over a period of 20 minutes. After the addition was complete, the reaction mixture was stirred at room temperature for 18 hours. The condenser and addition funnel were then replaced by a stopper and a Teflon valve adapter and the diethyl ether was removed by vacuum distillation at room temperature. The crude product, a trisneopentyl indium etherate mixture, was isolated by vacuum distillation at 110° C. into a side-arm flask (cooled to −196° C.) attached to the reaction flask by means of an 85° elbow. The distillation must be continued for approximately 8 hours. The diethyl ether was then removed from the crude trisneopentyl indium by simple vacuum distillation at room temperature for 12 hours. The product, a crystalline solid was finally purified by vacuum sublimation at 30° C. with the receiving flask at −10° C. The yield of purified trisneopentyl indium was 17.7 g (53.9 mmol, 92.4% based on indium triiodide).

In accordance with the above procedure, but using the corresponding bromides or chlorides in place of iodides with either or both reagents, the same product is obtained.

Trisneopentyl Indium Properties

Colorless, crystalline solid. M.p. 54°–55° C. Sublimes at 27° C., 0.01 mm. Anal. Calc: (Schwarzkopf Microanalytical Laboratory) C, 54.88; H, 10.15. Found: C, 54.71; H, 10.15. Hydrolysis: 3.02 mol $CMe_4$/mol trisneopentyl indium. Cryoscopic molecular weight, benzene solution, formula weight 328.21 (calc. m, obs MW) 0.0940, 311.8; 0.0628, 331.5; 0.0472, 338.1. $^1H$ NMR ($C_6H_6$ (7.13), δ), 1.11 (s, 27H, $CCMe_3$), 1.07 (s, 6H, $InCH_2$). IR (Nujol mull, cm$^{-1}$, relative intensity) bands of mulling agent omitted. 1379 s, 1371 s, 1228 vs, 1212 s, 1103 s, 1091 m, sh, 1007 s, 990 m, 922 w, 905 w, 800 vw, br, 734 m, 685 s, br, 570 s, 466 m, 372 m, 275 w, sh, 260 m, sh, 250 m, sh, 240 m, sh. Trisneopentyl indium is not pyrophoric but the compound is extremely sensitive to oxygen and water.

EXAMPLE III

Preparation of Methylbis(neopentyl)indium(III)

6.56 g (20.0 mmol) of trisneopentyl indium was reacted with 2.21 g (9.99 mmol) of indium chloride in refluxing diethyl ether for 48 hours to form bisneopentyl indium chloride. The resulting solution was filtered and then reacted with 30 mmol of methyl lithium (17.6 ml, 1.7M solution of diethyl ether) at 0° C. The methyl lithium solution was slowly added with stirring over a 10 minute time period. After the reaction mixture had stirred for 2 hours, the diethyl ether was removed by vacuum distillation. The product methyl bisneopentyl indium was separated from lithium chloride by extraction and filtration using 30 ml of pentane. Removal of pentane left a clear liquid product. In order to insure that the last traces of solvents (diethyl ether or pentane) had been removed, the sample was continuously evacuated for 3 hours at room temperature. Further purification was achieved by a vacuum distillation using a bath temperature of 80° C. and a head temperature of 55° C. The final purified product methyl bisneopentyl indium (3.35 g, 12.3 mmol) was isolated in 61.6% yield based on trisneopentyl indium.

Methyl Bisneopentyl Indium

Clear, colorless liquid, b.p. 55° C., −0.01 mm. Anal. Calcd. for methyl bisneopentyl indium: C, 48.58; H, 9.19. Found: C 48.72; H. 9.19 Cyroscopic molecular weight data, benzene solution formula weight 272, obsd. molality (obsd. mol. wt.): 0.0875 (320), 0.0598 (314), 0.0416 (314), 0.0306 (320), 0.0167 (322). $^1$H NMR (benzene, δ, reference benzene δ=7.13 ppm): −0.07 (3H, Me-In), 0.89 (4H, $CH_2$), 1.06 (18H, Me-C) IR (Neat liquid, cm$^{-1}$): 2958 (vs), 2905 (s), 2880 (s), 2860 (s), 1465 (m), 1457 (sh), 1382 (w), 1360 (m), 1260 (w), 1234 (m), 1109 (m), 1090 (m), 1055 (w), 1012 (m), 995 (w), 797 (w), 737 (w), 688 (m), 575 (w), 482 (m), 450 (w), 372 (w).

In accordance with the above procedure, but using trisneopentyl gallium in place of trisneopentyl indium, there is obtained methyl neopentyl gallium.

In accordance with the above procedure but where in place of a metallomethyl there is used a metalloethyl, there is obtained the corresponding ethyl bisneopentyl gallium or indium.

I claim:

1. $M[CH_2.C(CH_3)_3]X$ where X is chloro, bromo or iodo and M is selected from the group consisting of gallium and indium.

2. A compound of claim 1 where M=In and X is Cl.

3. A process of preparing a compound having the structure:

$$M[CH_2.C(CH_3)_3]_2R$$

wherein M is selected from the group consisting of Ga and In, and R=methyl or ethyl, which comprises reacting $(MX_3)$ with a trisneopentyl M compound, where X is halo selected from the group consisting of chloro, bromo or iodo in ethereal solution and reacting the product with (MT)R where (MT) is Li or MgX.

* * * * *